United States Patent
Moreno

[19]

[11] Patent Number: 6,082,826
[45] Date of Patent: Jul. 4, 2000

[54] PATIENT SUPPORT SYSTEM

[76] Inventor: Margaret Moreno, 6114 S. 295 Ct., Auburn, Wash. 98001

[21] Appl. No.: 09/234,700

[22] Filed: Jan. 21, 1999

[51] Int. Cl.$^7$ ..................................................... A47C 31/00
[52] U.S. Cl. ........................... 297/464; 297/465; 297/485
[58] Field of Search ................................... 297/464, 465, 297/216.1, 485

[56] References Cited

U.S. PATENT DOCUMENTS

| | | | |
|---|---|---|---|
| 4,541,425 | 9/1985 | Yetter, Jr. | 297/464 X |
| 4,807,937 | 2/1989 | Harrigan | 297/465 |
| 4,819,278 | 4/1989 | Ramos | 297/464 X |
| 4,846,528 | 7/1989 | Beier | 297/465 |
| 4,871,210 | 10/1989 | Alexander et al. | 297/485 |
| 5,042,878 | 8/1991 | Collins | 297/465 X |
| 5,547,250 | 8/1996 | Childers | 297/485 X |
| 5,626,397 | 5/1997 | Reid | 297/485 X |
| 5,829,840 | 11/1998 | Goeckel | 297/464 |

*Primary Examiner*—Peter M. Cuomo
*Assistant Examiner*—Stephen Vu

[57] ABSTRACT

A patient support system for holding the torso and head of a user upright when sitting in a wheel chair or a chair to prevent the user from falling off of the wheel chair or chair. The patient support system includes a vest harness designed for wear on the torso of a patient user. The vest harness has a neck opening, a pair of shoulder straps, a pair of side regions and a lower edge defining a lower opening. The vest harness has breaks through each of the shoulder straps and slits through each of the side regions of vest harness to define separable front and back portions of the vest harness. The front and back portions are detachably coupled together at the breaks of each of the shoulder straps and along the slits of each of the side regions. A chair structure is provided having a backrest and a seat. The back portion of the vest harness is detachably attachable to the backrest of the chair structure to help hold a patient user upright in the chair structure.

16 Claims, 5 Drawing Sheets

PATIENT SUPPORT SYSTEM

BACKGROUND OF THE INVENTION

1. Field of the Invention

The present invention relates to patient support systems and more particularly pertains to a new patient support system for holding the torso and head of a user upright when sitting in a wheel chair or a chair to prevent the user from falling off of the wheel chair or chair.

2. Description of the Prior Art

The use of patient support systems is known in the prior art. More specifically, patient support systems heretofore devised and utilized are known to consist basically of familiar, expected and obvious structural configurations, notwithstanding the myriad of designs encompassed by the crowded prior art which have been developed for the fulfillment of countless objectives and requirements.

Known prior art includes U. S. Pat. No. 2,851,033; U.S. Pat. No. 3,136,311; U.S. Pat. No. 5,154,487; U.S. Pat. No. 5,522,404; U.S. Pat. No. 5,664,844; and U.S. Pat. No. Des. 323,909.

While these devices fulfill their respective, particular objectives and requirements, the aforementioned patents do not disclose a new patient support system. The inventive device includes a vest harness designed for wear on the torso of a patient user. The vest harness has a neck opening, a pair of shoulder straps, a pair of side regions and a lower edge defining a lower opening. The vest harness has breaks through each of the shoulder straps and slits through each of the side regions of vest harness to define separable front and back portions of the vest harness. The front and back portions are detachably coupled together at the breaks of each of the shoulder straps and along the slits of each of the side regions. A chair structure is provided having a backrest and a seat. The back portion of the vest harness is detachably attachable to the backrest of the chair structure to help hold a patient user upright in the chair structure.

In these respects, the patient support system according to the present invention substantially departs from the conventional concepts and designs of the prior art, and in so doing provides an apparatus primarily developed for the purpose of holding the torso and head of a user upright when sitting in a wheel chair or a chair to prevent the user from falling off of the wheel chair or chair.

SUMMARY OF THE INVENTION

In view of the foregoing disadvantages inherent in the known types of patient support systems now present in the prior art, the present invention provides a new patient support system construction wherein the same can be utilized for holding the torso and head of a user upright when sitting in a wheel chair or a chair to prevent the user from falling off of the wheel chair or chair.

The general purpose of the present invention, which will be described subsequently in greater detail, is to provide a new patient support system apparatus and method which has many of the advantages of the patient support systems mentioned heretofore and many novel features that result in a new patient support system which is not anticipated, rendered obvious, suggested, or even implied by any of the prior art patient support systems, either alone or in any combination thereof.

To attain this, the present invention generally comprises a vest harness designed for wear on the torso of a patient user. The vest harness has a neck opening, a pair of shoulder straps, a pair of side regions and a lower edge defining a lower opening. The vest harness has breaks through each of the shoulder straps and slits through each of the side regions of vest harness to define separable front and back portions of the vest harness. The front and back portions are detachably coupled together at the breaks of each of the shoulder straps and along the slits of each of the side regions. A chair structure is provided having a backrest and a seat. The back portion of the vest harness is detachably attachable to the backrest of the chair structure to help hold a patient user upright in the chair structure.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new patient support system apparatus and method which has many of the advantages of the patient support systems mentioned heretofore and many novel features that result in a new patient support system which is not anticipated, rendered obvious, suggested, or even implied by any of the prior art patient support systems, either alone or in any combination thereof.

It is another object of the present invention to provide a new patient support system which may be easily and efficiently manufactured and marketed.

It is a further object of the present invention to provide a new patient support system which is of a durable and reliable construction.

An even further object of the present invention is to provide a new patient support system which is susceptible of a low cost of manufacture with regard to both materials and labor, and which accordingly is then susceptible of low prices of sale to the consuming public, thereby making such patient support system economically available to the buying public.

Still yet another object of the present invention is to provide a new patient support system which provides in the apparatuses and methods of the prior art some of the advantages thereof, while simultaneously overcoming some of the disadvantages normally associated therewith.

Still another object of the present invention is to provide a new patient support system for holding the torso and head of a user upright when sitting in a wheel chair or a chair to prevent the user from falling off of the wheel chair or chair.

Yet another object of the present invention is to provide a new patient support system which includes a vest harness designed for wear on the torso of a patient user. The vest harness has a neck opening, a pair of shoulder straps, a pair of side regions and a lower edge defining a lower opening. The vest harness has breaks through each of the shoulder straps and slits through each of the side regions of vest harness to define separable front and back portions of the vest harness. The front and back portions are detachably coupled together at the breaks of each of the shoulder straps and along the slits of each of the side regions. A chair structure is provided having a backrest and a seat. The back portion of the vest harness is detachably attachable to the backrest of the chair structure to help hold a patient user upright in the chair structure.

Still yet another object of the present invention is to provide a new patient support system that provides care providers with a means for releasably restraining a patient in a wheel chair or chair so that the patient will not injure themselves in the wheel chair or chair.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be made to the accompanying drawings and descriptive matter in which there are illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

With reference now to the drawings, and in particular to FIGS. 1 through 13 thereof, a new patient support system embodying the principles and concepts of the present invention and generally designated by the reference numeral 10 will be described.

As best illustrated in FIGS. 1 through 13, the patient support system 10 generally comprises a vest harness 11 designed for wear on the torso of a patient user 1. The vest harness has a neck opening 12, a pair of shoulder straps 13,14, a pair of side regions and a lower edge 15 defining a lower opening. The vest harness has breaks 16,17 through each of the shoulder straps and slits 18,19 through each of the side regions of vest harness to define separable front and back portions 20,21 of the vest harness. The front and back portions are detachably coupled together at the breaks of each of the shoulder straps and along the slits of each of the side regions. A chair structure 22 is provided having a backrest 23 and a seat 24. The back portion of the vest harness is detachably attachable to the backrest of the chair structure to help hold a patient user upright in the chair structure.

In use, the patient support system 10 is designed for supporting the torso and the head of a patient user upright in a chair structure such as a wheel chair or chair has a seat and a backrest. Specifically, the patient support system 10 comprises a vest harness 11 designed for wear on the torso of a patient user. The vest harness has a neck opening 12 designed for extending the neck of a patient user therethrough, a pair of shoulder straps 13,14 designed for hanging the vest on the shoulders of the patient user, a pair of side regions and a lower edge 15 defining a lower opening designed for extending the lower torso of the patient user therethrough. The vest harness has breaks 16,17 through each of the shoulder straps and slits 18,19 through each of the side regions of vest harness to define separable front and back portions 20,21 of the vest harness.

The front and back portions are detachably coupled together at the breaks of each of the shoulder straps and along the slits of each of the side regions. Preferably, hooks and loops fasteners detachably couple the front and back portions together at the breaks of each of the shoulder straps and along the slits of each of the side regions. The front and back portions of the vest harness have complementarily attachable strips 25,26,27,28 of the hooks and loops fastener provided thereon adjacent each break and slit of the vest harness.

Figures 12, 13:
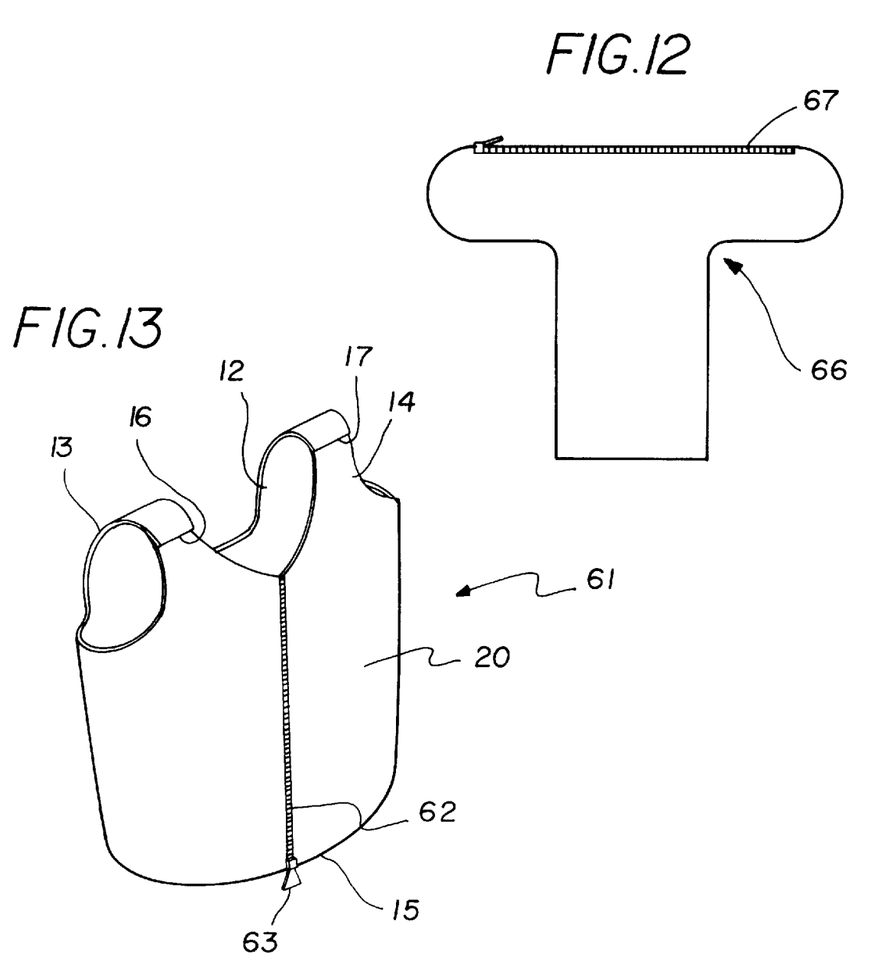
FIG. 12 is a schematic side view of a back rest pillow of the present invention.
FIG. 13 is a schematic front side view of another preferred embodiment vest harness of the present invention.

FIG. 13 illustrates another preferred embodiment of the vest harness 61 having integrally connected front and back portions. In this embodiment a front slit 62 is provided along the front portion with a zipper 63 coupling the sides of the front slit together.

Ideally, the front portion of the vest harness has a pocket 29 designed for holding items therein located adjacent the neck opening of the vest harness.

Figures 6, 7:
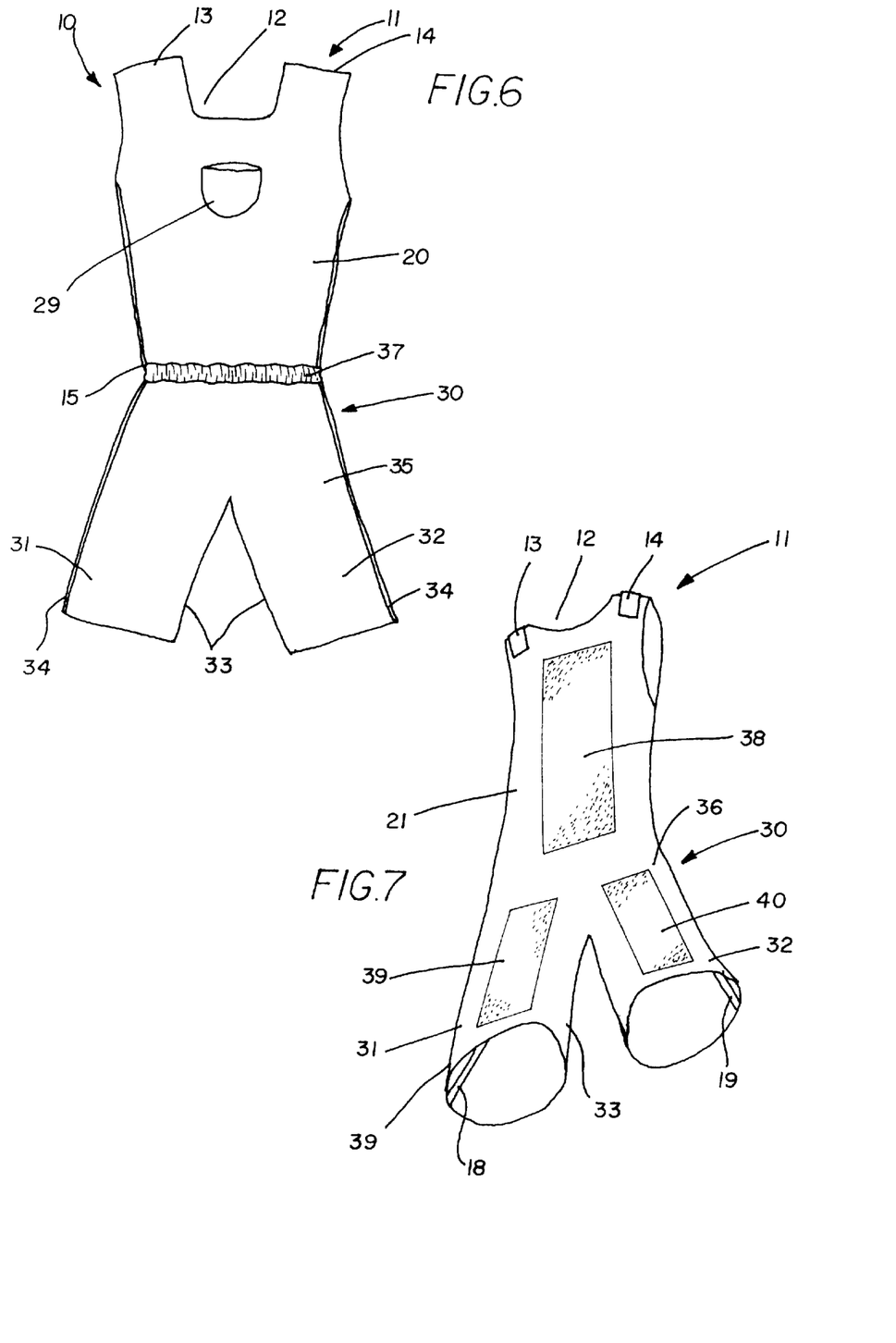
FIG. 6 is a schematic front side view of the vest harness embodiment with the shorts harness.
FIG. 7 is a schematic back side view of the vest harness embodiment with the shorts harness.

In a preferred embodiment, the vest harness has a shorts harness 30 designed for wear by a patient user is integrally coupled to the lower edge of the vest harness. The shorts harness has a pair of leg portions 31,32 each terminating at has a leg opening designed for extending the legs of the patient user therethrough. Each of the leg portions of the shorts harness has inner and outer side regions 33,34 with the inner side regions of the leg portions facing one another. The slits are further extended along the outer side regions of the leg portions to define forwards and rearwards portions 35,36 of the shorts harness.

The forwards and rearwards portions of the shorts harness are detachably coupled together along the slits. Preferably, hooks and loops fasteners detachably couple the forwards and rearwards portions together along the slits. The forwards and rearwards portions of the shorts harness have complementarily attachable strips of the hooks and loops fastener provided thereon adjacent each slit. Ideally, the complementarily attachable strips of the vest harness are further extended along the portions of the slit in the shorts harness.

Optionally, the front portion of the vest portion may have an elastic waist band 37 along the lower edge of the vest portion.

The back portion of the vest harness has a portion of a hooks and loops fastener 38 provided thereon in a generally rectangular pad covering at least one half on a total area of the back portion of the vest harness. Ideally, the portion of the hooks and loops fastener of the back portion of the vest harness comprises a hooks portion of a hooks and loops fastener. Each of the leg portions of the shorts harness preferably has a portion of a hooks and loops fastener 39,40 provided on the rearwards portion of the shorts harness each in a generally rectangular pad covering at least one half on a total area of the rearwards portion of the respective leg portion of the shorts harness. Ideally, the portion of the hooks and loops fastener of the legs portion of the shorts harness each comprise a hooks portion of a hooks and loops fastener.

Figure 8:
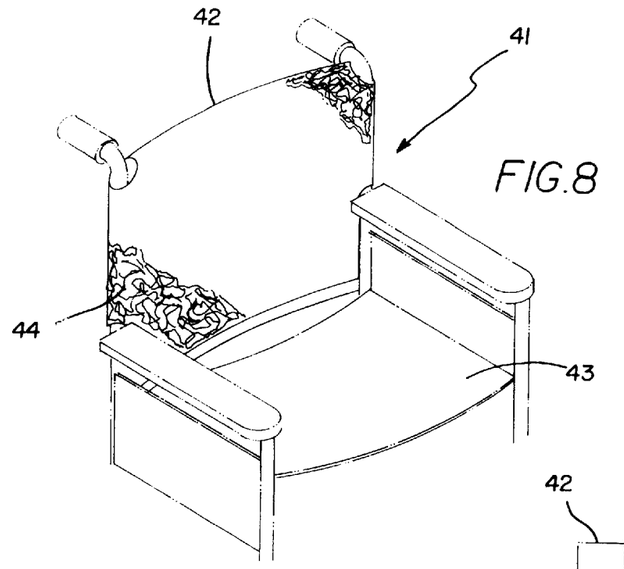
FIG. 8 is a schematic perspective view of a wheel chair structure of the present invention.

The system 10 also comprises a chair structure 41 with a backrest 42 and a seat 43. As illustrated, ideally, the chair structure comprises a wheel chair. The back portion of the vest harness is detachably attachable to the backrest of the chair structure to help hold a patient user upright in the chair structure. Ideally, the backrest of the chair structure has a cover 44 comprising a portion of a hooks and loops fastener complementarily attachable to the portion of the hooks and loops fastener of the back portion of the vest harness such that the portions of the hooks and loops fastener releasably engage one another to detachably attach the back portion of the vest harness to the back rest of the chair structure. Ideally, the portions of the hooks and loops fastener of the backrest of the chair structure comprises a loops portion of the hooks and loops fastener.

In the shorts harness embodiment, preferably the rearwards portion of the shorts harness is detachably attachable to the seat of the chair structure to help hold a patient user on the chair structure. Ideally, in this embodiment, the seat of the chair structure also has a cover comprising a portion of a hooks and loops fastener complementarily attachable to the portion of the hooks and loops fastener of the legs portion of the shorts harness such that the portions of the hooks and loops fastener releasably engage one another to detachably attach the rearwards portion of the shorts harness to the seat of the chair structure. Ideally, the portions of the hooks and loops fastener of the seat of the chair structure comprises a loops portion of the hooks and loops fastener.

Figure 9:
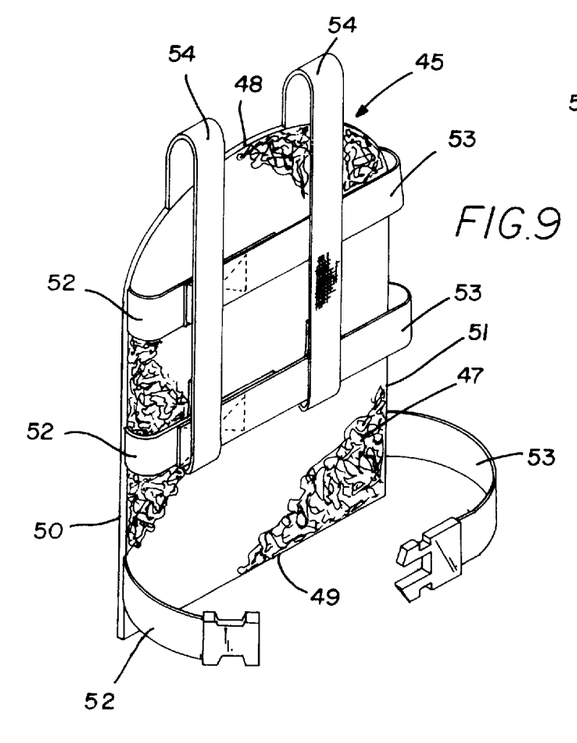
FIG. 9 is a schematic rear perspective view of the panel of the present invention.
Figure 10:
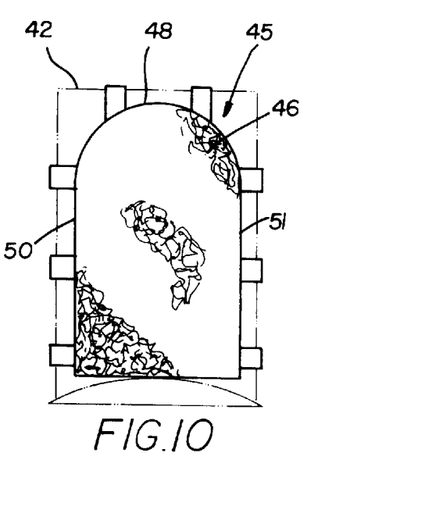
FIG. 10 is a schematic front side view of the panel of the present invention.

With reference to FIGS. 9 and 10, in another preferred embodiment, a panel 45 is provided having front and back faces 46,47, top and bottom edges 48,49, and a pair of side edges 50,51 extending between the top and bottom edges of the panel. The panel is mountable to a back rest of a chair structure. Each of the side edges of the panel has a plurality of side straps 52,53 coupled thereto. Each of the side straps of one the side edges of the panel is detachably attachable to an associated side strap of the other of the side edges of the panel preferably by hooks and loops fasteners or by a quick release fastener to the side straps located towards the bottom edge of the panel, to hold the panel to the backrest of a chair structure. The panel also preferably has a pair of upper straps 54 each with an end coupled to the top edge of the panel and detachably coupled by hooks and loops fasteners to one of the side straps of the side edges of the panel. In use, the upper straps are designed for hanging the panel over a top edge of a backrest of a chair structure.

In this embodiment of the system, the front and back faces of the panel each comprise a portion of a hooks and loops fastener complementarily attachable to the portion of the hooks and loops fastener of the back portion of the vest harness such that the portions of the hooks and loops fasteners releasably engage one another to detachably attach the back portion of the vest harness to the front face of the panel when mounted to the backrest of a chair structure. Ideally, the portion of the hooks and loops fastener of the panel comprises a loops portion of the hooks and loops fastener.

Figures 1, 2, 3:
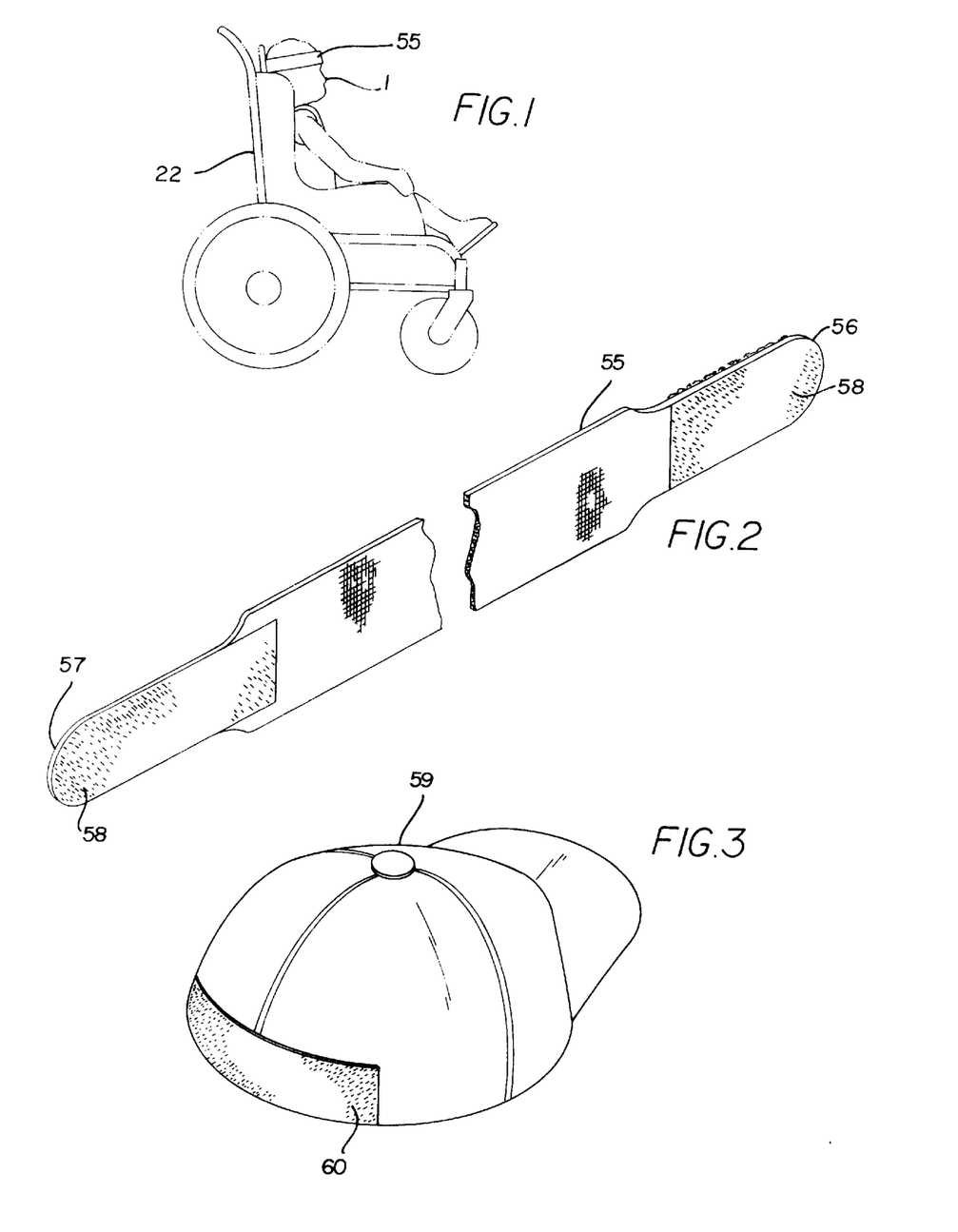
FIG. 1 is a schematic side view of a new patient support system according to the present invention.
FIG. 2 is a schematic perspective view of a head band of the present invention.
FIG. 3 is a schematic perspective rear view of a hat of the present invention.
Figure 4:
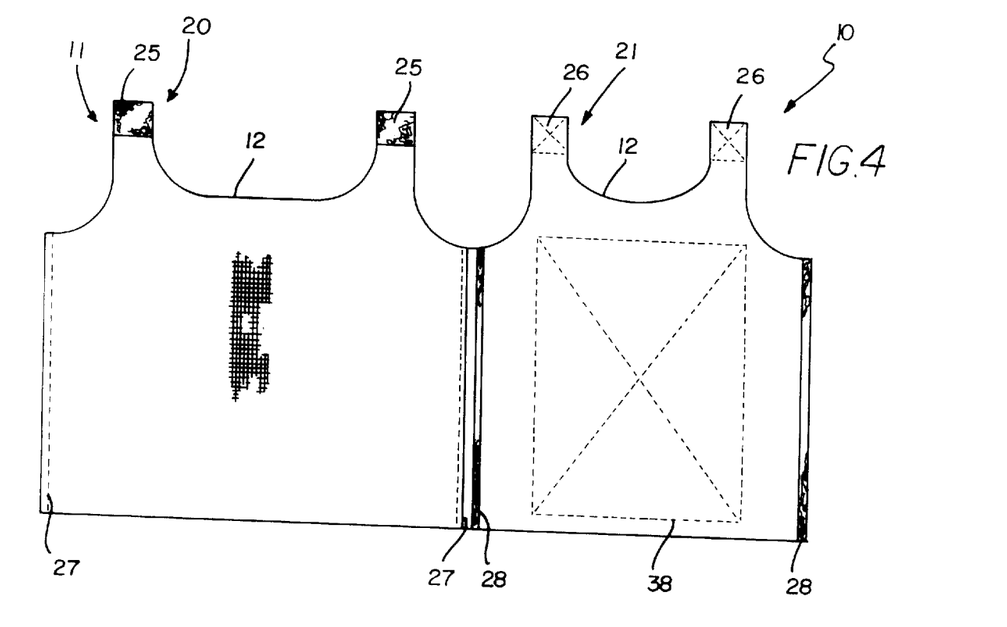
FIG. 4 is a schematic side view of the front and back portions of the vest harness of the present invention.
Figure 5:
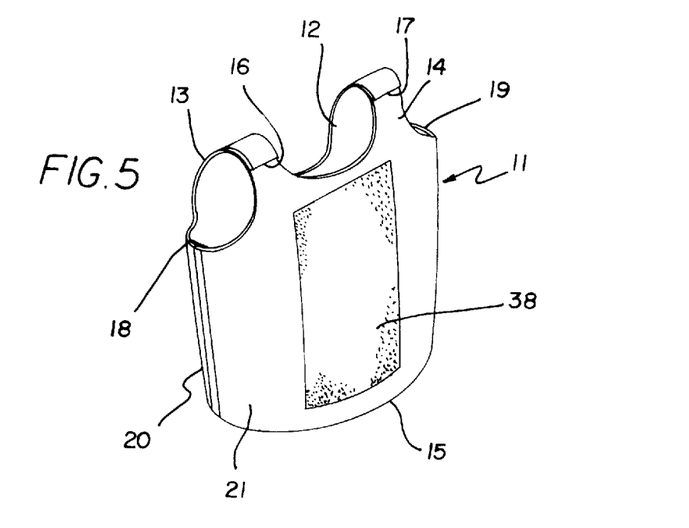
FIG. 5 is a schematic rear perspective view of the vest harness of the present invention.

With reference to Figures 1 and 2, the system preferably includes a flexible head band 55 with a pair of opposite ends 56,57 each having a hooks portion 58 of a hooks and loops fastener provided thereon. The hooks portions of the hooks and loops fastener of the ends of the head band are designed for attachment to the portion of a hooks and loops fastener of the backrest of the chair structure. As illustrated in FIG. 1, the head band is designed for securing the head of a patient user to the backrest of the chair structure. Optionally, instead of a head band, a hat 59 may be provided with a hooks portion 60 of a hooks and loops fastener provided at a back region of the hat. In use, the hooks portion of the hooks and loops fastener of the hat is designed for attachment to the portion of a hooks and loops fastener of the backrest of the chair structure, the hat is designed for securing the head of a patient user to the backrest of the chair structure.

Figure 11:
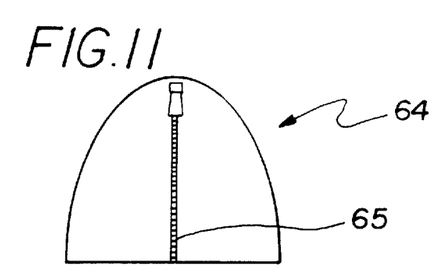
FIG. 11 is a schematic side view of a head rest cover of the present invention.

FIG. 11 illustrates a generally D-shaped head rest cover 64 that is adapted for covering the head rest of a child's chair of the type illustrated in FIG. 1. The head rest cover has a slit along its length that is coupled with a zipper 65 for aiding placement on and removal off of the head rest of the child's chair.

FIG. 12 illustrates a generally T-shaped pillow 66 having an upper zipper 67. The pillow is adapted for positioning between the backrest of the chair and the back of a child user.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A patient support system, comprising:

a vest harness adapted for wear on the torso of a patient user, said vest harness having a neck opening, a pair of shoulder straps, a pair of side regions and a lower edge defining a lower opening;

said vest harness having breaks through each of said shoulder straps and slits through each of said side regions of said vest harness to define separable front and back portions of said vest harness;

said front and back portions being detachably coupled together at said breaks of each of said shoulder straps and along said slits of each of said side regions;

a chair structure having a backrest and a seat;

said back portion of said vest harness being detachably attachable to said backrest of said chair structure to help hold a patient user upright in said chair structure; and wherein hooks and loops fasteners detachably couple said front and back portions together at said breaks of each of said shoulder straps and along said slits of each of said side regions.

2. The patient support system of claim 1, wherein said front and back portions of said vest harness have complementarily attachable strips of said hooks and loops fastener provided thereon adjacent each of said breaks and slits of said vest harness.

3. The patient support system of claim 2, wherein said front portion of said vest harness has a pocket located adjacent said neck opening of said vest harness.

4. The patient support system of claim 1, wherein said vest harness has a shorts harness coupled to said lower edge of said vest harness, said shorts harness having a pair of leg portions each having a leg opening.

5. The patient support system of claim 4, wherein each of said leg portions of said shorts harness has inner and outer side regions, said inner side regions of said leg portions facing one another, said slits being extended along said outer side regions of said leg portions to define forwards and rearwards portions of said shorts harness, said forwards and rearwards portions of said shorts harness being detachably coupled together along said slits.

6. The patient support system of claim 5, wherein hooks and loops fasteners detachably couple said forwards and rearwards portions together along said slits.

7. The patient support system of claim 1, wherein said back portion of said vest harness has a portion of a hooks and loops fastener provided thereon, wherein said backrest of said chair structure has a cover comprising a portion of a hooks and loops fastener complementarily attachable to said portion of said hooks and loops fastener of said back portion of said vest harness such that said portions of said hooks and loops fastener releasably engage one another to detachably attach said back portion of said vest harness to said back rest of said chair structure.

8. The patient support system of claim 7, wherein said portion of said hooks and loops fastener of said back portion of said vest harness comprising a generally rectangular pad covering at least one half on a total area of said back portion of said vest harness, wherein said portion of said hooks and loops fastener of said back portion of said vest harness comprises a hooks portion of a hooks and loops fastener, wherein said portions of said hooks and loops fastener of said backrest of said chair structure comprises a loops portion of said hooks and loops fastener.

9. A patient support system, comprising:

a vest harness adapted for wear on the torso of a patient user, said vest harness having a neck opening, a pair of shoulder straps, a pair of side regions and a lower edge defining a lower opening;

said vest harness having breaks through each of said shoulder straps and slits through each of said side regions of vest harness to define separable front and back portions of said vest harness;

said front and back portions being detachably coupled together at said breaks of each of said shoulder straps and along said slits of each of said side regions;

wherein hooks and loops fasteners detachably couple said front and back portions together at said breaks of each of said shoulder straps and along said slits of each of said side regions;

said front and back portions of said vest harness having complementarily attachable strips of said hooks and loops fastener provided thereon adjacent each of said and slits of said vest harness;

said front portion of said vest harness having a pocket adjacent said neck opening of said vest harness;

said vest harness having a shorts harness being coupled to said lower edge of said vest harness, said shorts harness having a pair of leg portions each having a leg opening;

each of said leg portions of said shorts harness having inner and outer side regions, said inner side regions of said leg portions facing one another;

said slits being extended along said outer side regions of said leg portions to define forwards and rearwards portions of said shorts harness;

said forwards and rearwards portions of said shorts harness being detachably coupled together along said slits, wherein hooks and loops fasteners detachably couple said forwards and rearwards portions together along said slits;

said back portion of said vest harness having a portion of a hooks and loops fastener provided thereon in a generally rectangular pad covering at least one half on a total area of said back portion of said vest harness, wherein said portion of said hooks and loops fastener of said back portion of said vest harness comprises a hooks portion of a hooks and loops fastener; and each of said leg portions of said shorts harness having a portion of a hooks and loops fastener provided on said rearwards portion of said shorts harness each in a generally rectangular pad covering at least one half on a total area of said rearwards portion of the respective leg portion of said shorts harness, wherein said portion of said hooks and loops fastener of said legs portion of said shorts harness each comprise a hooks portion of a hooks and loops fastener.

10. The patient support system of claim 9, further comprising a chair structure having a backrest and a seat, said back portion of said vest harness being detachably attachable to said backrest of said chair structure to help hold a patient user upright in said chair structure, wherein said backrest of said chair structure has a cover comprising a portion of a hooks and loops fastener complementarily attachable to said portion of said hooks and loops fastener of said back portion of said vest harness such that said portions of said hooks and loops fastener releasably engage one another to detachably attach said back portion of said vest harness to said back rest of said chair structure, wherein said portions of said hooks and loops fastener of said backrest of said chair structure comprises a loops portion of said hooks and loops fastener, said rearwards portion of said shorts harness being detachably attachable to said seat of said chair structure to help hold a patient user on said chair structure, wherein said seat of said chair structure has a cover comprising a portion of a hooks and loops fastener complementarily attachable to said portion of said hooks and loops fastener of said legs portion of said shorts harness such that said portions of said hooks and loops fastener releasably engage one another to detachably attach said rearwards portion of said shorts harness to said seat of said chair structure, and wherein said portions of said hooks and loops fastener of said seat of said chair structure comprises a loops portion of said hooks and loops fastener.

11. The patient support system of claim 10, wherein said chair structure comprises a wheel chair.

12. The patient support system of claim 9, further comprising a panel having front and back faces, top and bottom edges, and a pair of side edges extending between said top and bottom edges of said panel, said panel being mountable to a back rest of a chair structure, each of said side edges of said panel having a plurality of side straps coupled thereto, each of said side straps of one said side edges of said panel being detachably attachable to an associated side strap of the other of said side edges of said panel to hold said panel to the backrest of a chair structure, said panel having a pair of upper straps each having an end coupled to said top edge of said panel, and detachably coupled to one of said side straps of said side edges of said panel, said upper straps being adapted for hanging said panel over a top edge of a backrest of a chair structure, said front and back faces of said panel comprising a portion of a hooks and loops fastener complementarily attachable to said portion of said hooks and loops fastener of said back portion of said vest harness such that said portions of said hooks and loops fasteners releasably engage one another to detachably attach said back portion of said vest harness to said front face of said panel when mounted to the backrest of a chair structure, wherein said portion of said hooks and loops fastener of said panel comprises a loops portion of said hooks and loops fastener.

13. A patient support system, comprising:

a vest harness adapted for wear on the torso of a patient user, said vest harness having a neck opening, a pair of shoulder straps, a pair of side regions and a lower edge defining a lower opening;

said vest harness having breaks through each of said shoulder straps and slits through each of said side regions of vest harness to define separable front and back portions of said vest harness;

said front and back portions being detachably coupled together at said breaks of each of said shoulder straps and along said slits of each of said side regions;

a chair structure having a backrest and a seat;

said back portion of said vest harness being detachably attachable to said backrest of said chair structure to help hold a patient user upright in said chair structure; and wherein said vest harness has a shorts harness coupled to said lower edge of said vest harness, said shorts harness having a pair of leg portions each having a leg opening; and wherein each of said leg portions of said shorts harness has inner and outer side regions, said inner side regions of said leg portions facing one another, said slits being extended along said outer side regions of said leg portions to define forwards and rearwards portions of said shorts harness, said forwards and rearwards portions of said shorts harness being detachably coupled together along said slits.

14. The patient support system of claim 13, wherein hooks and loops fasteners detachably couple said forwards and rearwards portions together along said slits.

15. The patient support system of claim 13, wherein said back portion of said vest harness has a portion of a hooks and loops fastener provided thereon, wherein said backrest of said chair structure has a cover comprising a portion of a hooks and loops fastener complementarily attachable to said portion of said hooks and loops fastener of said back portion of said vest harness such that said portions of said hooks and loops fastener releasably engage one another to detachably attach said back portion of said vest harness to said back rest of said chair structure.

16. The patient support system of claim 15, wherein said portion of said hooks and loops fastener of said back portion of said vest harness comprising a generally rectangular pad covering at least one half on a total area of said back portion of said vest harness, wherein said portion of said hooks and loops fastener of said back portion of said vest harness comprises a hooks portion of a hooks and loops fastener, wherein said portions of said hooks and loops fastener of said backrest of said chair structure comprises a loops portion of said hooks and loops fastener.

* * * * *